United States Patent [19]

Sharpe et al.

[11] Patent Number: 5,391,175
[45] Date of Patent: Feb. 21, 1995

[54] METHOD OF USING AN ENDOKNOT PUSHER SURGICAL INSTRUMENT

[75] Inventors: Leslie A. Sharpe, Edina, Minn.; Francis C. Peterson, Prescott, Wis.

[73] Assignee: Sharpe Endosurgical Corporation, St. Paul, Minn.

[21] Appl. No.: 800,498

[22] Filed: Nov. 29, 1991

[51] Int. Cl.6 ............................................. A61B 17/00
[52] U.S. Cl. ................................... 606/148; 606/139
[58] Field of Search ........................ 606/148, 144, 139

[56] References Cited

U.S. PATENT DOCUMENTS

| | | |
|---|---|---|
| 1,991,316 | 2/1935 | Gage . |
| 2,146,673 | 2/1939 | Frisone . |
| 2,595,086 | 4/1952 | Larzelere . |
| 3,476,114 | 11/1969 | Shannon et al. . |
| 3,609,790 | 10/1971 | Butch . |
| 3,834,395 | 9/1974 | Santos . |
| 3,871,379 | 3/1975 | Clarke .................. 606/148 |
| 4,018,229 | 4/1977 | Komiya . |
| 4,509,516 | 4/1985 | Richmond ............. 606/148 |
| 4,545,373 | 10/1985 | Christoudias ......... 606/148 |
| 4,602,635 | 7/1986 | Mulhollan et al. ... 606/148 |
| 4,614,187 | 9/1986 | Mulhollan et al. ... 606/148 |
| 4,935,027 | 6/1990 | Yoon ..................... 606/146 |
| 5,053,043 | 10/1991 | Gottesman et al. ... 606/148 |

*Primary Examiner*—Stephen C. Pellegrino
*Assistant Examiner*—Jeffrey A. Schmidt
*Attorney, Agent, or Firm*—Merchant, Gould, Smith, Edell, Welter & Schmidt

[57] ABSTRACT

A surgical instrument for positioning and tying knots during endoscopic surgery is provided with an elongate shaft having a ligature restraining aperture for accepting a strand of the ligature.

3 Claims, 5 Drawing Sheets

METHOD OF USING AN ENDOKNOT PUSHER SURGICAL INSTRUMENT

FIELD OF THE INVENTION

The present invention is a knot pushing surgical instrument for endoscopic procedures. The instrument is used to position and tighten knots formed in ligatures during endoscopic surgery.

BACKGROUND OF THE INVENTION

Knot pushing and positioning instruments are known in the art. U.S. Pat. No. 2,595,086 to LARZELERE, discloses a ring-shaped structure having an open slot. In use, a ligature is placed around an anatomical structure and both strands of the ligature are positioned on the periphery of a slotted ring structure. The knot itself is positioned in a slot formed in the ring and the slack strands are taken up together as the knot is pushed onto an anatomical structure. The ring structure is attached to a rod which is used to manipulate the tool and to push the knot into position.

FIG. 10 shows the working end of another prior art knotpushing device referred to as the Clarke-Reich ligator, which is distributed by Marlow Surgical Technologies, and which is intended for endoscopic use. This structure shows an aperture which communicates to the outside of the instrument through a slot. In use, one strand of the ligature is placed in the aperture by passing it through the slot. The tool is pushed causing the knot to slip over itself as it moves into position.

Open structures as taught by this prior art are difficult to use, since the instrument may slip off the ligature. Such structures can also have a tendency to become tangled with the knot and are not useful for untangling a knot. The seat of the Clarke-Riech ligator is particularly problematical when it engage an open loop of a loosely tied knot. The geometry of this device prevents knots from being effectively tightened. Also, the conventional use of the Clarke-Reich ligator on secondary knots frays the ligature which weakens it. Most surgeons do not prefer tools which form loose knots in frayed ligature. These problems have collectively spawned the development of the endoscopic surgical stapler.

SUMMARY OF THE INVENTION

In contrast to these prior art structures, the present knot pusher invention permits the surgeon to tie a multiple throw surgeon's knot, tighten it properly and secure this primary knot with a series of well formed secondary hitches. The structure of the present invention includes a closed aperture located at the working end of an elongated rod. A relief is formed at the location of the aperture to provide a volume or clearance space to locate and protect the knot as it is pushed through the percutaneous port into the surgical field. A T-shaped handle is provided to facilitate use.

BRIEF DESCRIPTION OF THE DRAWING

Throughout the figures of the drawing, identical reference numerals refer to identical structure, wherein.

DETAILED DESCRIPTION OF THE PREFERRED EMBODIMENT

Figure 1:
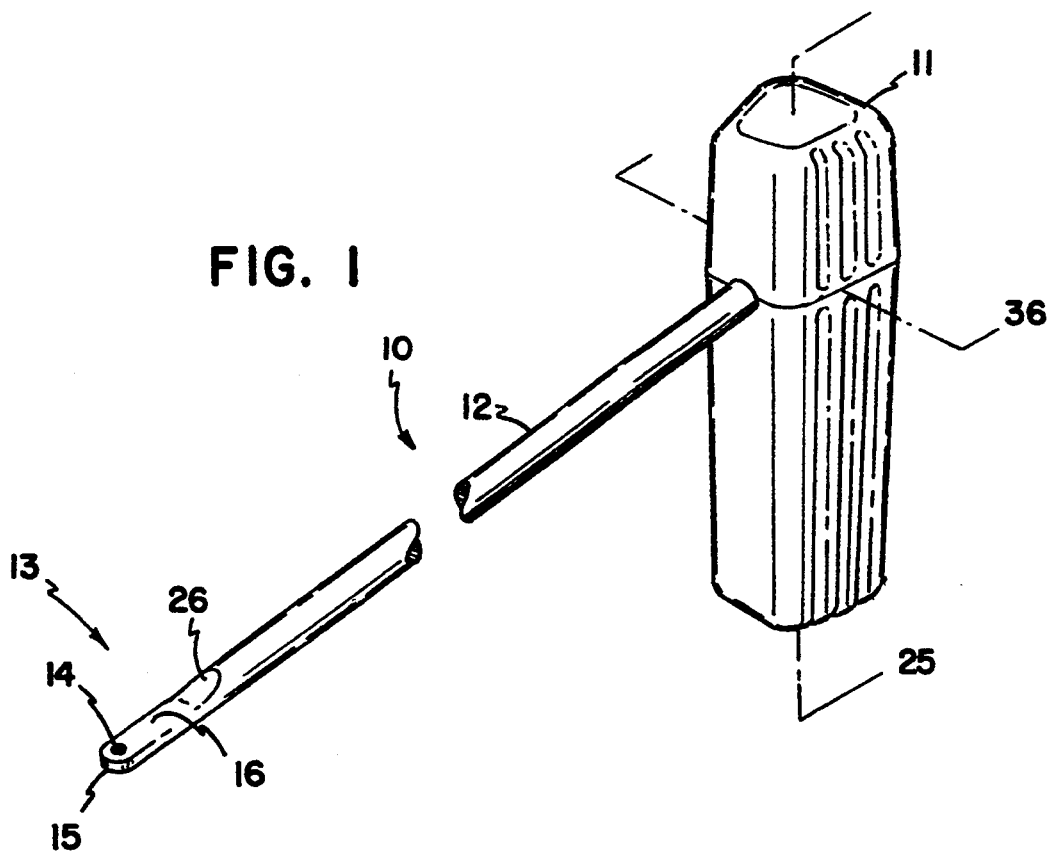
FIG. 1 is a perspective view of the surgical instrument.
Figure 10:
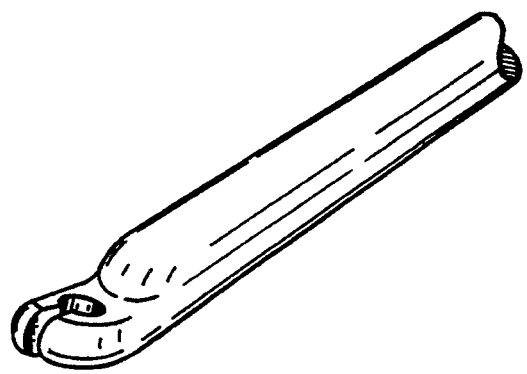
FIG. 10 depicts the prior art structure of the Clarke-Reich ligator.

FIG. 1 shows a perspective view of the endoknot pusher. The endoknot surgical instrument 10 has a substantially T-shaped handle 11, which is preferably manufactured from medical grade polysulfone plastic. This handle 11 structure is molded onto an elongated stainless steel shaft or rod 12, which is preferably 6.5 millimeters in diameter, and approximately 30 centimeters in length. The working end 13 of the instrument includes a ligature restraining aperture 14 formed proximate the tip 15 of the instrument. A scalloped relief 16 is formed adjacent or proximate the ligature restraining aperture 14 to provide and define a knot reception volume 26.

The ligature restraining aperture 14 is completely deburred and chamfered or rounded to prevent snagging of the ligature passed through the restraining aperture 14. The ligature restraining aperture 14 has a completely closed periphery with a preferred diameter of 0.125 inches. The tip 15 of the instrument is partially hemispheric, with a preferred radius of approximately 0.125 inches, and is therefore blunt. This ligature restraining aperture 14 must be threaded with the ligature in operation.

Figure 2:
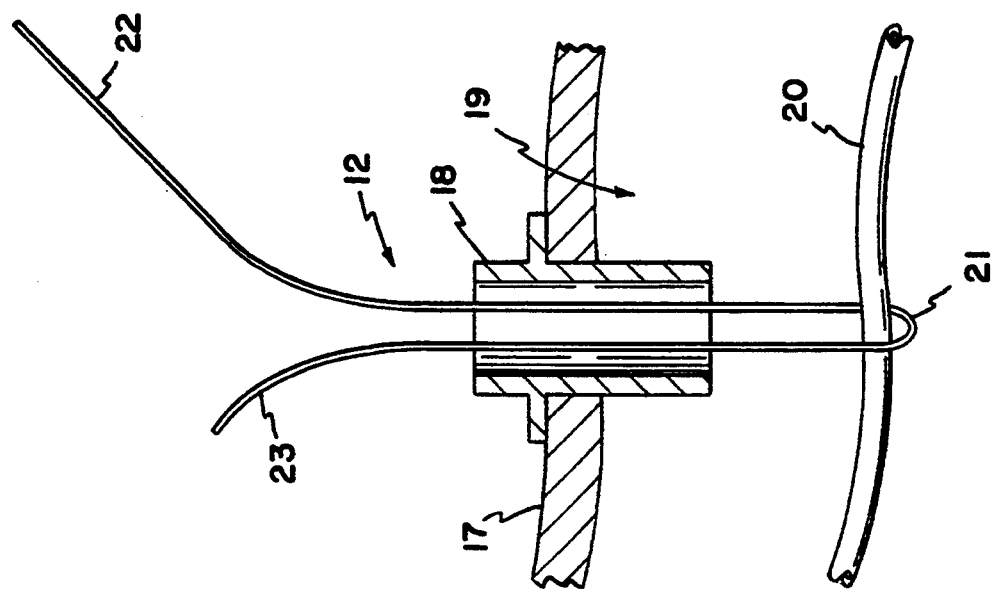

FIG. 2 is a highly schematic view, depicting the surgical field where the endoknot surgical instrument 10 is used. The patient's abdominal wall 17 has been punctured with a trocar, and an endoscopic access port 18 has been placed in the wall, providing communication to the abdominal cavity 19. The cavity 19 contains an internal anatomical or prosthetic structure 20 such as a pedicle, vascular structure or suture ring for ligation. The surgeon utilizes tools to place the ligature 21 around the internal anatomical structure 20, passing the free standing strand 22 captive and the tying strand 23 out of the same percutaneous port 18.

Figure 3:
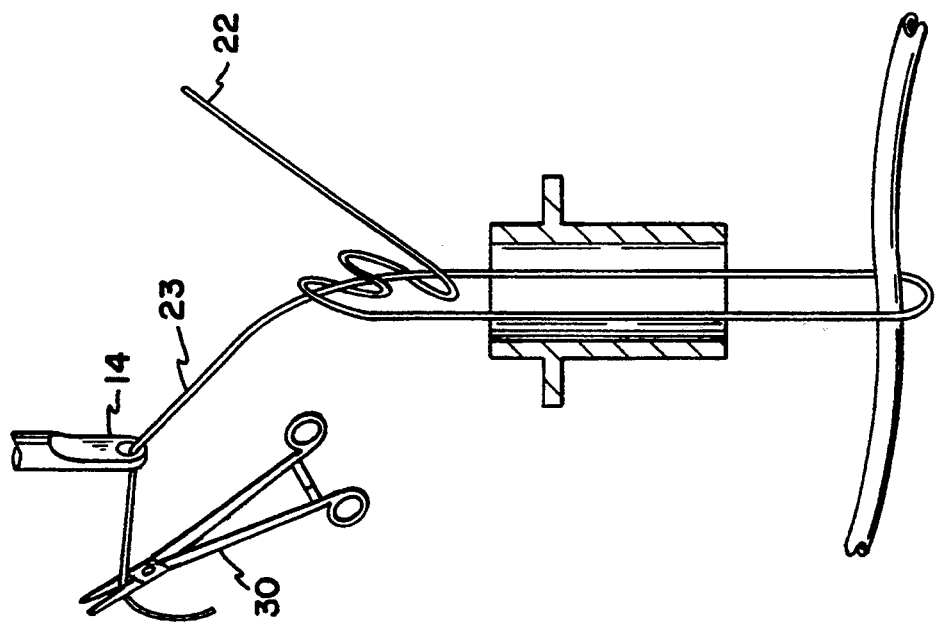
FIG. 2, FIG. 3, FIG. 4 and FIG. 5 depict a sequence of operations, showing the use of the surgical instrument of FIG. 1 to place and tighten a primary knot.
Figure 5:
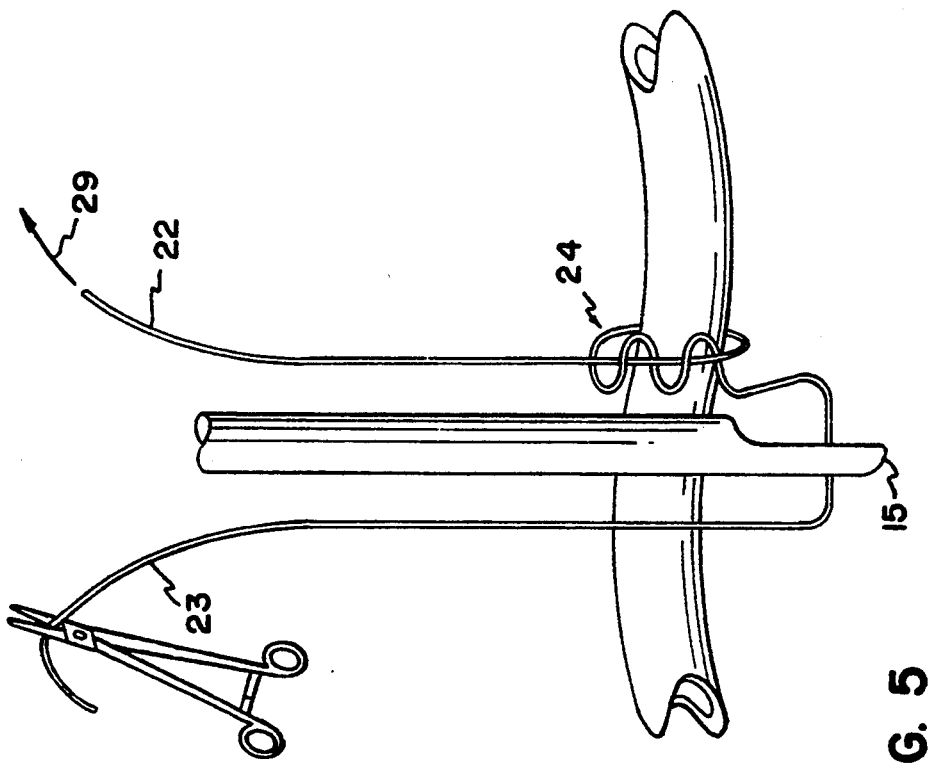
Figure 4:
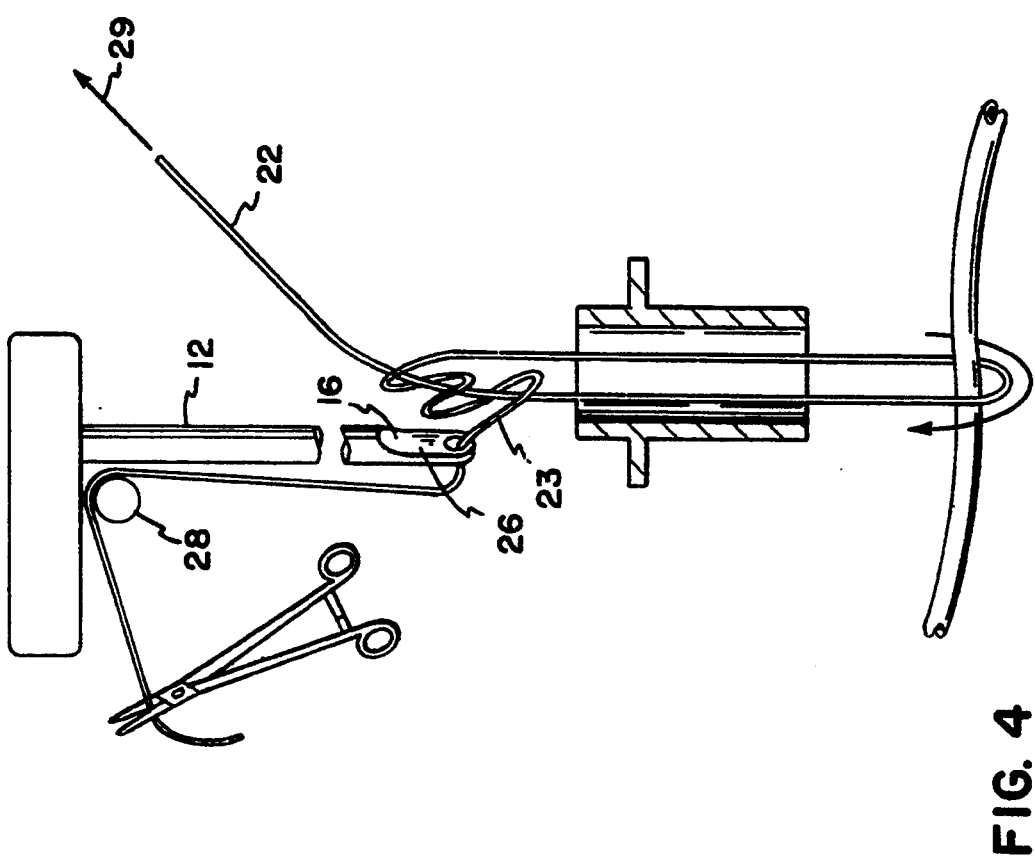

FIG. 3 should be considered together with FIG. 4 and FIG. 5. Together, the figures show a procedure for tying a primary surgeon's knot 24. In FIG. 3 the surgeon has formed a classic double throw surgeon's knot 24 in the captive tying strand 23, by winding it around the free standing strand 22. This knot 24 is formed extracorporally. After knot 24 formation, the surgeon threads the captive tying strand 23 into the restraining aperture 14 of the endoknot pusher surgical instrument 10. It is highly preferred to tag the terminal end of the captive tying strand 23 with a forceps as indicated by forceps 30. In use the surgeon may hold the endoknot pusher instrument 10 in his hand, and the forceps 30 on the strand 23 apply slight traction to the standing strand 22 to transfer the knot 24 to the tying strand 23 as shown in FIG. 4, and to prevent the knot from becoming tangled.

In FIG. 4 the bubble 28 indicates that the surgeon presses the tying strand 23 against the rod 12, as the rod 12 and tying strand 23 are is advanced toward the anatomical internal structure 20. During this process the knot 24 lies adjacent the relief 16, trailing behind the restraining aperture 14. In practice, the knot 24 is quite small and lies in contact with the relief 16, within the knot reception volume 26.

FIG. 5 depicts the advancement of the rod through the port (not shown). In the figure, the knot 24 has been positioned on the anatomical structure 20 and the tip 15 is pushed pass the structure 20 to tighten the knot 24. During this process the standing stand 22 is withdrawn away from the anatomical structure 20 as indicated by arrow 29 to take up the slack. With this knot 24 tightened, the strands 22 and 23 are no longer capable of relative motion past the anatomical internal structure 20. This prevents the passage of another surgeon's knot onto the ligature 21. However additional security hitches or other secondary knots may be placed to secure the surgeon's knot 24 as shown in connection with FIG. 6, FIG. 7, and FIG. 8.

Figure 7:
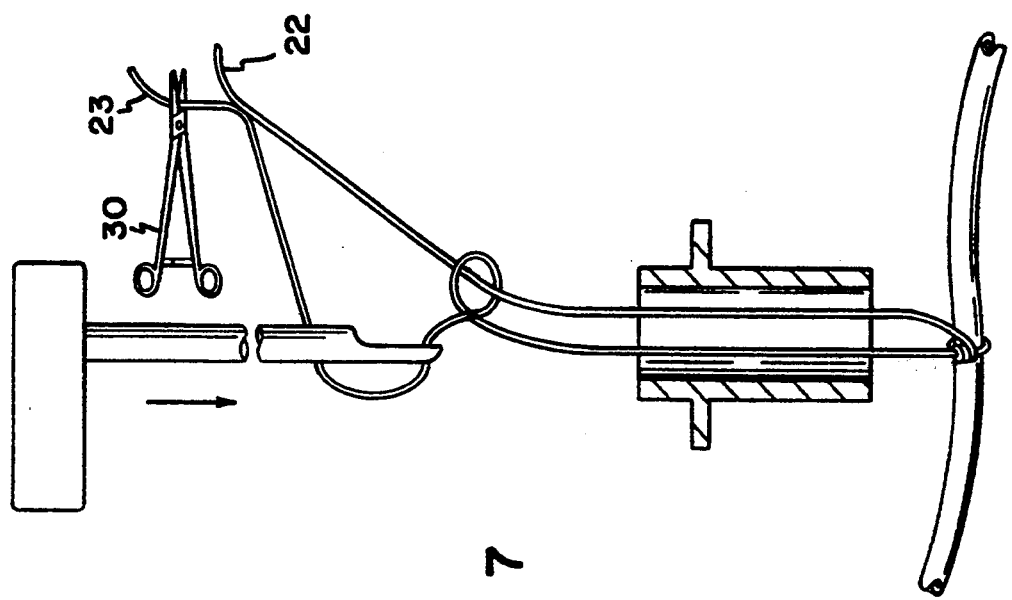
FIG. 6, FIG. 7, and FIG. 8 depict a sequence of operations, showing the use of the surgical instrument of FIG. 1 to place and tighten a secondary knot.
Figure 6:
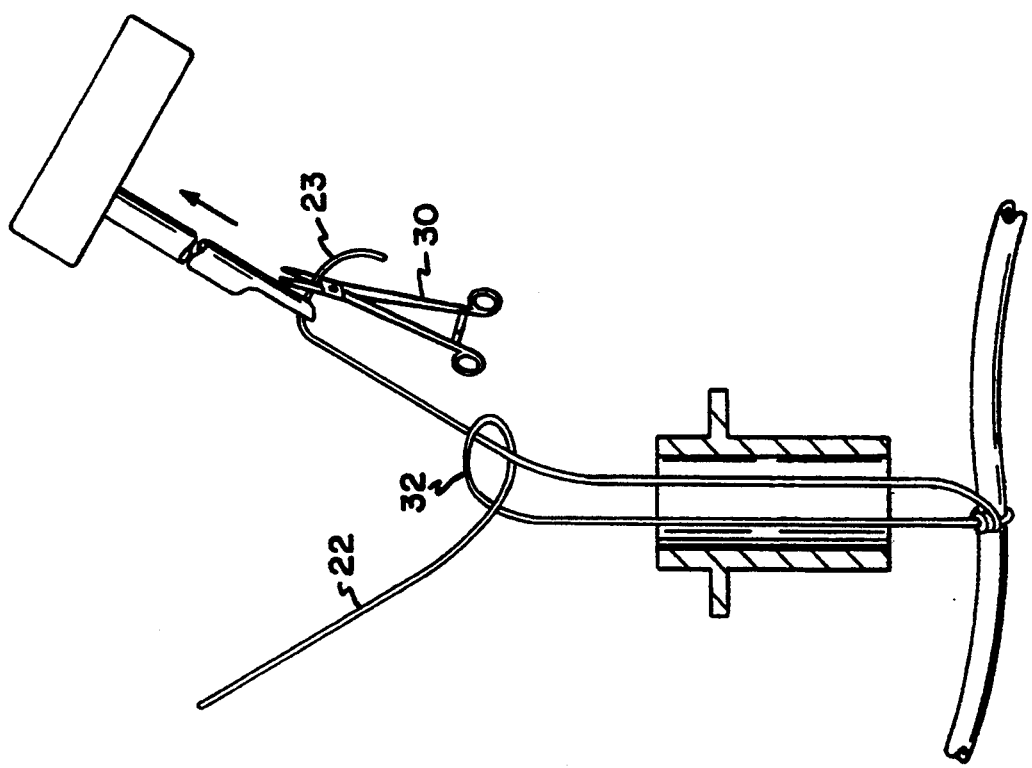
Figure 9:
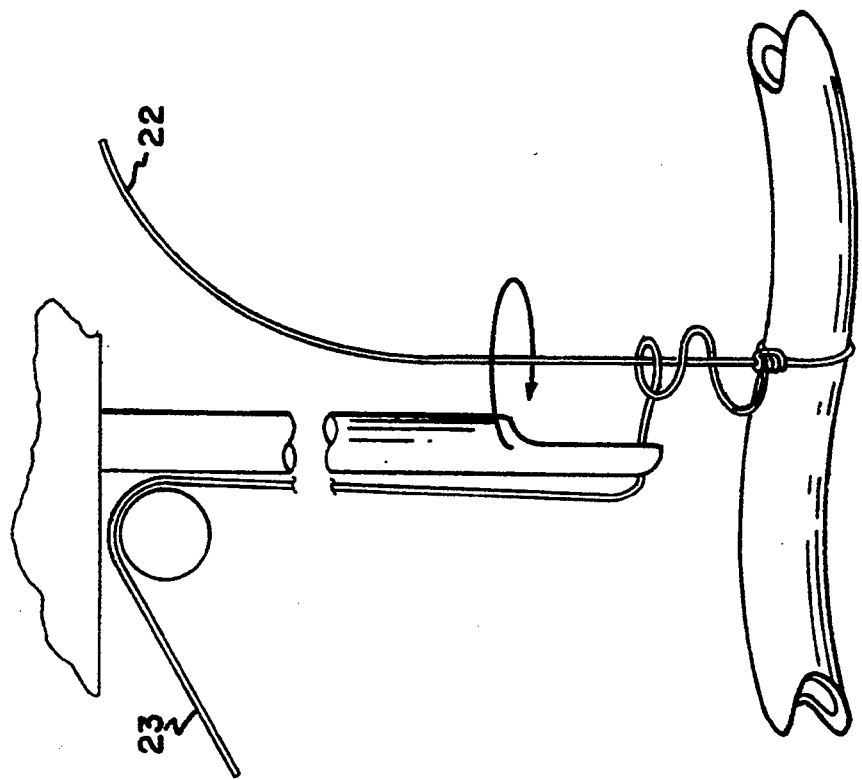
FIG. 9 shows how the instrument of FIG. 1 can be used to de-tangle knots.
Figure 8:
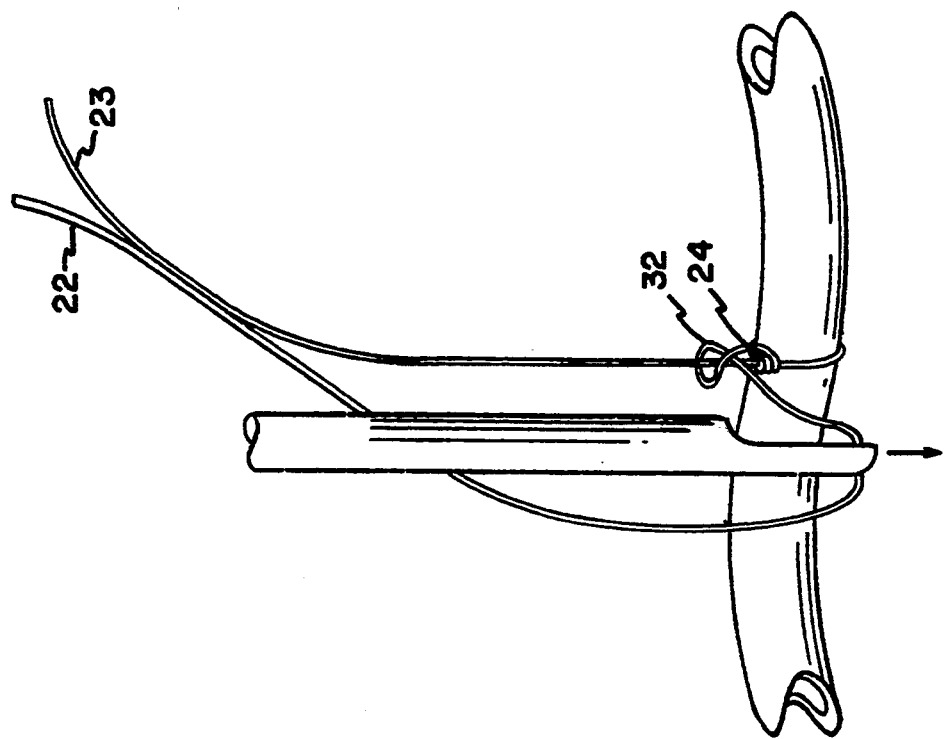

In FIG. 6 the captive tying strand is tagged with a forceps. Slight traction is applied to the tying strand 23 to permit formation of a simple hitch 32 in the standing strand 22. In practice, this hitch is easily formed while the surgeon grasps the endoknot pusher surgical instrument 10 in one hand. This practice speeds hitch formation by the surgeon. Next, the surgeon moves the free standing strand 22 and the captive tying strand 23 together and holds them both in one hand with a slight amount of slack in the captive tying strand 23 as shown in FIG. 7. This grasping action is depicted in the figure. Next, the surgeon inserts the endoknot pusher surgical instrument 10 through the port 18 and pushes the handle. This is depicted in FIG. 8. Since the strands 22 and 23 are immobile with respect to each other at the primary knot 24 and at the surgeon's hand, the hitch 32 slides over itself as it is passed through the port and into contact with the primary knot 24. During passage of the hitch through the port 18, the hitch lies in contact with the relief 16 as the ligature 21 slides through the knot restraining aperture 14. Advancement of the endoknot pusher past the primary knot 24. As shown in FIG. 7, tightens the hitch 32 onto the primary knot 24.

Although the preferred primary knot 24 is the surgeon's knot which is the preferred primary knot for most surgical procedures, other knots may be used with great facility. In a similar fashion, the preferred secondary knot 32 is shown as a simple hitch 32 but other knots may be used as well.

The fact that the ligature 21 strand is captive or trapped in the ligature restraining aperture 14 of the instrument, permits the surgeon to positively control the tying strand 23 with one hand throughout the tying procedure. If the surgeon "lets go" of the instrument intentionally or accidentally, the captive strand will not disengage or come off the instrument 10. Thus the captive strand provides instant orientation to the surgeon as to which strand is which during the knot tying operation. This helps the surgeon to develop a variety of methods to un-tangle knots or to place additional knots or hitches on the ligature without twisting.

The T-shaped handle 11 is small and has a bilateral symmetry around the plane shown in FIG. 1 by reference line 25. This handle permits use of the tool by both right and left-handed surgeons with equal facility. The handle is asymmetrical in the plane defined by section lines 36 which be provides an indication of the angular orientation of the relief 16 and the ligature restraining aperture 14. This provides a visual and tactile reference to the physician outside of the surgical field. Although other handle shapes are contemplated within the scope and spirit of the invention they should be ambidextrous with an indexing structure to permit instinctive orientation of the relief within the surgical field. Also although variations on the aperture and relief are possible it is important to ensure that the relationship between the handle and relief be preserved.

What is claimed is:

1. A method of ligating an internal structure comprising the steps of:
    (a) passing a ligature around the internal structure;
    (b) extracting the strands of said ligature through a single percutaneous port;
    (c) defining a free standing strand and defining a captive tying strand;
    (d) tying a knot in said captive tying strand wherein said knot engages said free standing strand;
    (e) threading said captive tying strand through a knot restraining aperture having a closed periphery, said aperture formed in an elongate rod, said elongate rod having a knot reception volume formed proximate said aperture, such that said knot is positioned within said knot reception volume;
    (f) holding said captive tying strand against said rod;
    (g) advancing said knot, said rod, and said captive tying strand together into position adjacent said internal structure;
    (h) applying traction to said knot by holding said rod and said captive tying strand together and by pushing said rod and captive tying strand past said structure while holding said captive tying strand stationary, thereby tightening said knot.

2. A method of ligating an internal structure with a primary knot comprising the steps of:
    (a) passing a ligature around the internal structure;
    (b) extracting the strands of said ligature through a single percutaneous port;
    (c) defining a free standing strand and a captive tying strand;
    (d) tying a multiple throw knot in said captive tying strand wherein said knot engages said free standing strand;
    (e) threading said captive tying strand through a knot restraining aperture having a closed periphery, said aperture formed in an elongate rod, said elongate rod having a knot reception volume formed proximate said aperture, such that said knot is positioned within said knot reception volume;
    (f) holding said captive tying strand against said rod;
    (g) advancing said knot, said rod, and said captive tying strand together into position adjacent said internal structure;
    (h) applying traction to said knot by holding said rod and said captive tying strand together and by pushing said rod and said captive tying strand past said structure, while withdrawing said free standing strand from said port, thereby tightening said knot.

3. A method of securing a primary knot placed on an internal structure with a secondary knot comprising the steps of:
    (a) forming a primary knot on a ligature passed around the internal structure;
    (b) extracting the strands of said ligature through a single percutaneous port;
    (c) defining a free standing strand and a captive tying strand;
    (d) applying traction to said captive tying strand;
    (e) tying a single throw knot in said free standing strand wherein said knot engages said free standing strand;

(f) applying traction to said free standing strand whereby said knot is transferred to said captive tying stand;

(g) threading said captive tying strand through a knot restraining aperture having a closed periphery, said aperture formed in an elongate rod, said elongate rod having a knot reception volume formed proximate said aperture, such that said knot is positioned within said knot reception volume;

(h) forming slack in said captive tying strand;

(i) holding said captive tying strand against said free standing strand;

(j) advancing said knot, said rod, along the length of said captive tying strand to position said knot adjacent said internal structure;

(k) applying traction to said knot by holding said captive tying strand and said free standing strand together and by pushing said rod past said structure thereby tightening said knot.

* * * * *

UNITED STATES PATENT AND TRADEMARK OFFICE
CERTIFICATE OF CORRECTION

PATENT NO. : 5,391,175

DATED : February 21, 1995

INVENTOR(S) : Sharpe et al.

It is certified that error appears in the above-identified patent and that said Letters Patent is hereby corrected as shown below:

In column 1, line 37, please delete the word "seat", and insert therefor --slot--

In column 1, line 37, please delete the name "Riech", and insert therefor --Reich--

In column 1, line 38, please delete the word "engage", and insert therefor --engages--

In column 2, line 44, please delete the words "captive and the", and insert therefor --and the captive--

In column 2, line 65, before the words "is advanced", please delete the word "are"

In column 3, line 63, before the word "provides", please delete the word "be"

Signed and Sealed this

Twentieth Day of June, 1995

Attest:

BRUCE LEHMAN

Attesting Officer    Commissioner of Patents and Trademarks